(12) United States Patent
Brown et al.

(10) Patent No.: US 11,008,157 B2
(45) Date of Patent: May 18, 2021

(54) VESSELS AND METHODS FOR CRYOPRESERVATION

(71) Applicant: CORNING INCORPORATED, Corning, NY (US)

(72) Inventors: Jessica Monique Brown, Rye, NH (US); Nicholas Michael Illsley, Tewksbury, MA (US); Gregory Roger Martin, Acton, ME (US); Ana Marie del Pilar Pardo, Portsmouth, NH (US); Allison Jean Tanner, Portmouth, NH (US)

(73) Assignee: Corning Incorporated, Corning, NY (US)

( * ) Notice: Subject to any disclaimer, the term of this patent is extended or adjusted under 35 U.S.C. 154(b) by 518 days.

(21) Appl. No.: 15/419,678

(22) Filed: Jan. 30, 2017

(65) Prior Publication Data
US 2017/0135337 A1 May 18, 2017

Related U.S. Application Data

(62) Division of application No. 14/081,326, filed on Nov. 15, 2013, now abandoned.
(Continued)

(51) Int. Cl.
*B65D 83/00* (2006.01)
*A01N 1/02* (2006.01)
(Continued)

(52) U.S. Cl.
CPC ....... *B65D 83/0072* (2013.01); *A01N 1/0242* (2013.01); *A01N 1/0263* (2013.01);
(Continued)

(58) Field of Classification Search
CPC ............ B65D 83/0072; B65D 83/0005; B65D 83/0022; B65D 83/005; B65D 83/0055;
(Continued)

(56) References Cited

U.S. PATENT DOCUMENTS 2,157,476 A    5/1939  Brodesser
2,434,505 A    1/1948  Miller
(Continued)

FOREIGN PATENT DOCUMENTS

AU    2010241296 B2    9/2014
CA       2314658 A1    1/2002
(Continued)

OTHER PUBLICATIONS

International Searching Authority; Patent Cooperation Treaty; International Search Report and Written Opinion; International Application No. PCT/US2014/050483; dated Feb. 18, 2015; pp. 1-20.
(Continued)

*Primary Examiner* — James N Smalley
*Assistant Examiner* — Jennifer Castriotta
(74) *Attorney, Agent, or Firm* — Annie J. Kock

(57) ABSTRACT

An article including either a frame having an interior cavity, and a flexible liner situated within the interior cavity; or a deformable frame having an interior cavity. Either frame can receive a sample, such as liquid having suspended live cells, and cooling freezes the sample to a solid sample. The solid sample can be readily ejected from the article having either a frame with the flexible liner, or the deformable frame, without extensive thawing. The solid sample can be rapidly displaced from the article.

12 Claims, 12 Drawing Sheets

Related U.S. Application Data

(60) Provisional application No. 61/866,785, filed on Aug. 16, 2013.

(51) Int. Cl.

| | | |
|---|---|---|
| *A61J 1/14* | (2006.01) | |
| *A61J 1/05* | (2006.01) | |
| *A61J 1/16* | (2006.01) | |
| *B65D 81/32* | (2006.01) | |
| *B65D 21/02* | (2006.01) | |
| *C12M 1/26* | (2006.01) | |
| *C12M 1/00* | (2006.01) | |
| C12M 3/00 | (2006.01) | |
| A61M 5/145 | (2006.01) | |
| A61M 5/24 | (2006.01) | |

(52) U.S. Cl.
CPC ......... *A01N 1/0268* (2013.01); *A01N 1/0273* (2013.01); *A01N 1/0284* (2013.01); *A61J 1/05* (2013.01); *A61J 1/1412* (2013.01); *A61J 1/16* (2013.01); *B65D 21/0206* (2013.01); *B65D 81/325* (2013.01); *B65D 83/0005* (2013.01); *B65D 83/005* (2013.01); *B65D 83/0022* (2013.01); *B65D 83/0033* (2013.01); *B65D 83/0038* (2013.01); *B65D 83/0055* (2013.01); *B65D 83/0077* (2013.01); *C12M 33/04* (2013.01); *C12M 45/22* (2013.01); A61M 5/145 (2013.01); A61M 5/2425 (2013.01); C12M 23/48 (2013.01)

(58) Field of Classification Search
CPC ............ B65D 83/0033; B65D 83/0038; B65D 83/0077; B65D 81/325; B65D 21/0206; B65D 21/0201; A01N 1/0263; A01N 1/0273
USPC .................................... 220/23.2, 23.8, 23.83
See application file for complete search history.

(56) References Cited

U.S. PATENT DOCUMENTS

| | | | |
|---|---|---|---|
| 2,992,501 A * | 7/1961 | Douglas .................. B44D 3/14 | 211/73 |
| 3,139,208 A * | 6/1964 | Irwin ...................... B44D 3/00 | 206/1.8 |
| 3,166,221 A | 1/1965 | Nielson | |
| 3,419,179 A | 12/1968 | Deuschle et al. | |
| 3,483,908 A * | 12/1969 | Donovan .................. B65D 1/34 | 206/526 |
| 3,491,907 A | 1/1970 | Eelkema | |
| 3,727,802 A | 4/1973 | Schnurmacher | |
| 3,810,503 A | 5/1974 | Lewis, Jr. et al. | |
| 3,827,602 A * | 8/1974 | Nicholls ............. B65D 81/325 | 222/137 |
| 4,018,222 A | 4/1977 | McAleer et al. | |
| 4,251,995 A | 2/1981 | Pert et al. | |
| 4,560,535 A * | 12/1985 | Bouchee ............. B01L 3/50855 | 422/552 |
| 4,639,250 A | 1/1987 | Rycroft | |
| 4,880,125 A | 11/1989 | LeBeau | |
| 4,972,969 A | 11/1990 | Randklev | |
| 5,033,631 A | 7/1991 | Nightingale | |
| 5,699,935 A * | 12/1997 | Stahley ............... B65D 81/325 | 222/105 |
| 5,711,446 A | 1/1998 | Jeffs et al. | |
| 5,826,751 A | 10/1998 | Stahley et al. | |
| 5,873,490 A | 2/1999 | Walpole | |
| 6,315,171 B1 * | 11/2001 | Piscopo ............... B65D 81/325 | 222/386 |
| 6,337,205 B1 | 1/2002 | Wisniewski | |
| 6,379,342 B1 | 4/2002 | Levinson | |
| 6,446,860 B1 | 9/2002 | Robichaud | |
| 8,092,878 B2 | 1/2012 | Miller et al. | |
| 8,168,138 B2 | 5/2012 | Che et al. | |
| 8,222,027 B2 | 7/2012 | Woods et al. | |
| 8,550,273 B2 | 10/2013 | Levin et al. | |
| 8,834,014 B2 | 9/2014 | Summons et al. | |
| 2002/0056716 A1 | 5/2002 | Banhagel | |
| 2002/0197656 A1 | 12/2002 | Li et al. | |
| 2004/0097862 A1 | 5/2004 | Lampeter et al. | |
| 2004/0217080 A1 * | 11/2004 | Renz .................. A61J 9/00 | 215/11.3 |
| 2005/0124965 A1 | 6/2005 | Haywood | |
| 2006/0019233 A1 | 1/2006 | Yaghmour | |
| 2008/0118686 A1 | 5/2008 | Glasgow et al. | |
| 2009/0194904 A1 | 8/2009 | Logel et al. | |
| 2009/0236258 A1 | 9/2009 | Connell | |
| 2009/0255938 A1 | 10/2009 | Fuja | |
| 2009/0305224 A1 | 12/2009 | He et al. | |
| 2010/0196873 A1 | 8/2010 | Woods | |
| 2010/0241074 A1 | 9/2010 | Bivin et al. | |
| 2010/0316446 A1 | 12/2010 | Runyon | |
| 2011/0008908 A1 | 1/2011 | Biesbrouck | |
| 2011/0143452 A1 | 6/2011 | Che et al. | |
| 2011/0174814 A1 | 7/2011 | Ortiz et al. | |
| 2011/0250632 A1 | 10/2011 | Tatnell et al. | |
| 2011/0295212 A1 * | 12/2011 | Greter .............. A61B 17/00491 | 604/191 |
| 2012/0027895 A1 | 2/2012 | Bach | |
| 2012/0029471 A1 | 2/2012 | Lee et al. | |
| 2012/0258214 A1 | 10/2012 | Sagel | |
| 2013/0065301 A1 | 3/2013 | Woods et al. | |
| 2014/0079898 A1 | 3/2014 | Kaushik et al. | |
| 2014/0138406 A1 | 5/2014 | Sanfilippo et al. | |
| 2014/0157798 A1 | 6/2014 | Jimenez-Rios et al. | |
| 2014/0158695 A1 | 6/2014 | Jimenez-Rios | |
| 2014/0224808 A1 | 8/2014 | Brisard | |
| 2015/0048085 A1 | 2/2015 | Brown et al. | |
| 2016/0363362 A1 | 12/2016 | Chen | |
| 2017/0172140 A1 | 6/2017 | Schaefer | |
| 2018/0242572 A1 | 8/2018 | Coddaire et al. | |
| 2018/0242573 A1 | 8/2018 | Lacey et al. | |

FOREIGN PATENT DOCUMENTS

| | | |
|---|---|---|
| CH | 240683 A | 1/1946 |
| CN | 2892068 Y | 4/2007 |
| CN | 201284338 Y | 8/2009 |
| CN | 201322489 Y | 10/2009 |
| CN | 102379278 A | 3/2012 |
| CN | 202522460 U | 11/2012 |
| CN | 203290150 U | 11/2013 |
| CN | 203519403 U | 4/2014 |
| CN | 204599132 U | 9/2015 |
| CN | 104986426 A | 10/2015 |
| EP | 2191899 A1 | 6/2010 |
| EP | 2364928 A1 | 9/2011 |
| EP | 2442857 A1 | 4/2012 |
| EP | 2575442 A1 | 4/2013 |
| FR | 1411842 A | 9/1965 |
| FR | 2846128 A1 | 4/2004 |
| JP | 07-333219 A | 12/1995 |
| JP | 10-309185 A | 11/1998 |
| JP | 2000516137 A | 12/2000 |
| JP | 2001106262 A | 4/2001 |
| JP | 2003267463 A | 9/2003 |
| JP | 2004018504 A | 1/2004 |
| JP | 2006516398 A | 7/2006 |
| JP | 2008-507563 A | 3/2008 |
| JP | 2010-518393 A | 5/2010 |
| JP | 04848755 B2 | 12/2011 |
| JP | 04876922 B2 | 2/2012 |
| JP | 2012020763 A | 2/2012 |
| JP | 2012-219017 A | 11/2012 |
| JP | 2014-190904 A | 10/2014 |
| WO | 1999001770 A1 | 1/1999 |
| WO | 2000030703 A1 | 6/2000 |
| WO | 2001043869 A2 | 6/2001 |
| WO | 0228733 A1 | 4/2002 |
| WO | 2005022996 A1 | 3/2005 |

(56) References Cited

FOREIGN PATENT DOCUMENTS

| WO | 2006012613 A1 | 2/2006 |
|---|---|---|
| WO | 2006059626 A1 | 6/2006 |
| WO | 2007103917 A2 | 9/2007 |
| WO | 2008/097091 A1 | 8/2008 |
| WO | 2010/145786 A1 | 12/2010 |
| WO | 2011146998 A1 | 12/2011 |
| WO | 2013171483 A1 | 11/2013 |
| WO | 2014/095840 A1 | 6/2014 |
| WO | 2014088859 A1 | 6/2014 |
| WO | 2015/023560 A2 | 2/2015 |
| WO | 2016040063 A1 | 3/2016 |
| WO | 2017/087176 A1 | 5/2017 |
| WO | 2017/087178 A1 | 5/2017 |

OTHER PUBLICATIONS

English Translation of Office Action in Japanese Patent Application No. 2016-534764 dated May 29, 2018; 8 Pages; Japanese Patent Office.

Corning 1.2mL External Threaded Polypropylene Cryogenic Vial, Self-Standing With Conical Bottom (Product #430658) Corning Life Sciences Catalong, Jan. 24, 2015, https://catalog2.corning.com/LifeSciences/en-US/Shopping/ProductDetails.aspx?productid=430658.

* cited by examiner

VESSELS AND METHODS FOR CRYOPRESERVATION

CLAIMING BENEFIT OF PRIOR FILED U.S. APPLICATIONS

This application is a divisional of U.S. patent application Ser. No. 14/081,326 filed on Nov. 15, 2013, which claims the benefit of priority under 35 U.S.C. § 119 of U.S. Provisional Application Ser. No. 61/866,785, filed on Aug. 16, 2013, both of which are relied upon and incorporated herein by reference in their entirety.

The entire disclosure of any publication or patent document mentioned herein is incorporated by reference.

BACKGROUND

The disclosure generally relates to cryopreservation vessels and methods of making and using the vessels for cryopreservation.

SUMMARY

In embodiments, the disclosure provides cryopreservation vessels or containers, and methods of making and using the vessels for cryopreservation of, for example, biological material. The disclosed cryopreservation vessels have a deformable interior chamber for: receiving a liquid sample; freezing the liquid sample to a solid sample; and conveniently and efficiently dispensing the cryopreserved solid sample into another vessel for further processing such as reconstitution.

BRIEF DESCRIPTION OF THE DRAWINGS

In embodiments of the disclosure.

DETAILED DESCRIPTION

Figure 1A:
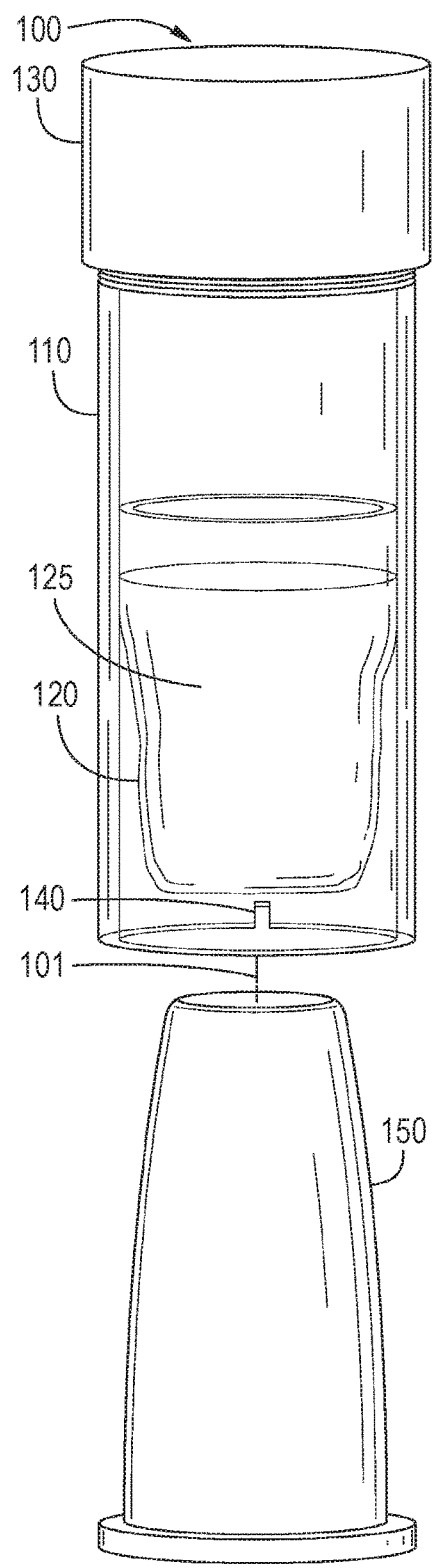
FIG. 1A illustrates aspects of an exemplary article (100) such as a cryotube.

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

In embodiments, the disclosed article and the disclosed method of making and using the article provide one or more advantageous features or aspects, including for example as discussed below. Features or aspects recited in any of the claims are generally applicable to all facets of the invention. Any recited single or multiple feature or aspect in any one claim can be combined or permuted with any other recited feature or aspect in any other claim or claims.

Definitions

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described event, circumstance, or component, can or cannot occur, and that the description includes instances where the event, circumstance, or component, occurs and instances where it does not.

The indefinite article "a" or "an" and its corresponding definite article "the" as used herein means at least one, or one or more, unless specified otherwise.

Abbreviations, which are well known to one of ordinary skill in the art, may be used (e.g., "h" or "hrs" for hour or hours, "g" or "gm" for gram(s), "mL" for milliliters, and "rt" for room temperature, "nm" for nanometers, and like abbreviations).

Specific and preferred values disclosed for components, ingredients, additives, dimensions, conditions, and like aspects, and ranges thereof, are for illustration only; they do not exclude other defined values or other values within defined ranges. The articles and methods of the disclosure can include any value or any combination of the values, specific values, more specific values, and preferred values described herein, including explicit or implicit intermediate values and ranges.

Cryopreservation is a process that freezes cells or tissues at a very low temperature to reduce damage due to chemical and biological activity. A biological material is placed in medium with a cryoprotectant, and the combination is pipetted into a cryovial of glass or cryotube of plastic that can withstand freezing at liquid nitrogen temperature (−196° C.). Generally, mammalian cells require a controlled rate of freezing at approximately 1° C. per minute. This usually occurs in an article that permits this rate of freezing when placed in a −80° C. freezer for 24 hours. Following this treatment, the cryotube or cryovial can be placed in liquid nitrogen gas phase (−152° C.). Users would rather not be concerned with where the cryotube is placed within the liquid nitrogen containment vessel. However, occasionally liquid nitrogen can seep into cryotubes and cryovials. As the cells are quickly warmed to maintain viability during the thawing procedure, the liquid nitrogen contaminant in the cryotube or cryovial rapidly becomes nitrogen gas that expands, and can rupture the cryotube or cryovial.

A traditional method for thawing frozen biological material is, for example: 1) the cryotube or cryovial of biological material is removed from the liquid nitrogen containment vessel; 2) the cryotube or cryovial is taken to a 37° C. water bath and continually swirled to quickly thaw the biological material (Cells can lose viability due to osmotic changes and the presence of the cryoprotectant if the thawing period is too slow. How quickly the cells lose viability depends on the cell type); and 3) the thawed biological material is pipetted out of the cryotube or cryovial and placed in culture medium. The culture medium, in a large enough volume to significantly reduce the cryoprotectant concentration, may be in a vessel that will be used for the cell culture, or the medium may be in a centrifuge tube so that the cryoprotectant can be removed following centrifugation to separate the cryoprotectant from the cell pellet.

A cryopreservation container that reduces the risk of container rupture, reduces the risk of contamination, and increases biological material viability, would be beneficial to workers in the cell culture industry.

In embodiments, the disclosure provides an article comprising:
a frame, e.g., a tube or like housing having, for example, a rigid or inflexible property, a highly flexible reversible or deformable property, or an intermediate flexibility or bendability property between rigid and highly flexible, having an interior cavity; and
a flexible liner situated within the interior cavity and optionally attached to a portion of the frame such as the exterior of the frame or within the interior cavity of the frame;
the frame has a first open end for receiving a liquid sample into the flexible liner, and a closure member, e.g., screw cap, press fit plug, snap fit plug, or like members, for reversibly sealing the received liquid sample in the interior cavity, and the frame has a second open end, for engaging, for example, a holder for the article or, alternatively, for receiving an ejector to displace the flexible liner and the sample contents from a first location within the cavity.

In embodiments, the frame can be, for example, a hollow cylinder or hollow conic having first and second open ends.

In embodiments, the liner in the interior cavity can be, for example, a biodegradable flexible liner.

In embodiments, the closure member can be, for example, at least one of: a screw cap adapted to engage screw threads on the frame; a press fit plug having a strap to engage the frame, or a combination thereof.

In embodiments, the frame can be, for example, a plurality of frames, the flexible liner can be, for example, a plurality of flexible liners, the ejector can be, for example, a plurality of ejectors, and the closure member can be, for example, a plurality of closure members.

In embodiments, the ejector can be, for example, integral with the article; worn by an operator; attached to an external support; or a combination thereof.

In embodiments, if the ejector is integral with the article, the ejector comprises at least one retractable member, see for example, FIGS. 7A-D, 8A-D, and 9.

In embodiments, the article can further comprise a holster where the holster holds the article and permits the closure member to be removed with, for example, a single human hand or a single mechanical gripper. The holster can have, for example, a recessed volume that conforms to the volume of at least a portion of the base of the article's frame at the second end, and the holster can have a detent feature to engage the article's frame to restrict rotational freedom of the article's frame.

In embodiments, the article having a liner can further comprise at least one ejector member.

In embodiments, the disclosure provides an article comprising:
a flexible frame, that is a reversibly deformable and resilient body, having an interior cavity, and the frame has a first open end for receiving a liquid sample into the interior cavity and an optional closure member for reversibly sealing the received liquid sample in the interior cavity, and the frame has a second closed end for engaging a holder for the frame. The flexible frame embodiment can eject the frozen sample from the interior cavity of the frame without the need of inserting an ejector member (i.e., free of an ejector member). The interior cavity can have, for example, a hollow cylindrical geometry and the base of the cylinder can be orientated at the first open end, or a hollow conical geometry and the base of the conic can be orientated at the first open end.

In embodiments, the second closed end for engaging a holder for the frame can be, for example, an indentation in the wall of the frame.

In embodiments, the disclosure provides a method of using the above disclosed article having a frame and flexible liner, comprising:
filling the cavity defined by the flexible liner of the article with a liquid sample;
sealing the article, for example, with a suitable closure;
cooling the filled sealed article to convert the liquid sample to a solid sample; and
ejecting the solid sample from the liner in the cavity of the article into a receiving vessel with an ejector.

In embodiments, the above method can further comprise storing the solid sample, prior to ejecting, for a period of time at cryogenic temperatures, such as from about 0.5 minutes to 20 years, and like time intervals, including intermediate values and ranges.

In embodiments, the ejecting of the solid sample from the liner in the cavity of the article can be accomplished by, for example, inserting or actuating an ejector member into the article.

In embodiments, the ejecting the solid sample from the article can be accomplished without substantial intermediate thawing, for example, the ejecting can be accomplished, for example, without immersion of the article or the solid sample in a thawing bath, without the article or the solid sample standing at ambient temperature for more than a brief period, such as from 10 seconds to 5 minutes, from 30 seconds to 2 minutes, and like periods, including intermediate values and ranges, or combinations thereof.

In embodiments, the disclosure provides a method of using the above disclosed article having a flexible frame comprising, for example:
filling the interior of the article with a liquid sample;
sealing the article with a suitable closure;
cooling the filled sealed article to convert the liquid sample to a solid sample; and
ejecting the solid sample from the article into a receiving vessel by manually or mechanically compressing or squeezing the flexible frame of the article.

In embodiments, the above method can also further comprise storing the solid sample, prior to ejecting, for a period of time at cryogenic temperatures, such as from about 0.5 minutes to 20 years, and like time intervals, including intermediate values and ranges.

In embodiments, ejecting the solid sample from this flexible walled article, as in the related article embodiment having a flexible interior liner, can also be accomplished without substantial intermediate thawing.

In embodiments, the compressing or squeezing the flexible or deformable frame body can be accomplished with, for example, a human hand, a mechanical device, a robot, and like instrumentalities, or a combination thereof.

In embodiments, the disclosure provides a cryopreservation kit comprising:
a cryopreservation article having an interior cavity for holding a liquid or solid sample, and a closure for sealing, e.g., gas and liquid tight, the sample in the interior cavity of the article;
a holster for holding the article;
if the frame of the article is rigid and has a flexible liner, then: an ejector for ejecting a frozen sample, i.e., the work piece, for the interior of the article; and
instructions for use of the article.

"Consisting essentially of" or "consisting of" in embodiments can refer to, for example:
An article having one or more of the disclosed aspects as defined herein, such as:
a frame having an interior cavity; and
a flexible liner situated within the frame's interior cavity;
the frame has a first open end for receiving a liquid sample into the flexible liner, and a closure member for reversibly sealing the received liquid sample in the interior cavity, and the frame has a second open end, for engaging a holder for the article, and for receiving an ejector to displace the flexible liner and the sample contents from a location within the cavity.
A method of using the above article having the flexible liner having one or more of the disclosed steps as defined herein, such as:
filling the liner of the article with a liquid sample;
sealing the article;
cooling the filled sealed article to convert the liquid sample to a solid sample;
storing the solid sample for a period of time at cryogenic temperatures, such as from about 0.5 minutes to 20 years, and
ejecting the solid sample from the article with an ejector into a receiving vessel.
An article having one or more of the disclosed aspects as defined herein, such as:
a flexible or reversibly deformable frame having an interior cavity, and the frame has a first open end for receiving a liquid sample into the interior cavity, but no flexible liner or free of a flexible liner, and a closure member for reversibly sealing the received liquid sample in the interior cavity, and the frame has a second closed end for engaging a holster for the frame.
A method of using the above liner-free article having the flexible frame having one or more of the disclosed steps as defined herein, such as:
filling the interior of the article having a flexible reversibly deformable frame with a liquid sample;
sealing the article;
cooling the filled sealed article to convert the liquid sample to a solid sample; storing the solid sample for a period of time at cryogenic temperatures, such as from about 0.5 minutes to 20 years, and
ejecting the solid sample from the article into a receiving vessel by manually or mechanically squeezing or compressing the flexible frame or deformable body of the article.
A cryopreservation kit having one or more of the disclosed aspects as defined herein, such as:
a cryopreservation article having an interior cavity for a liquid or solid sample, and a closure for sealing the sample in the interior cavity of the article;
a holster for holding the article;
if the frame of the article is flexible and reversibly deformable and is with or without a liner, then ejecting a frozen sample for the interior of the article by, for example, squeezing or compressing the frame; and
instructions for use of the article.

The article, the method of making the article, and the method of using the article, of the disclosure can include the components or steps listed in the claim, plus other components or steps that do not materially affect the basic and novel properties of the compositions, articles, apparatus, or methods of making and use of the disclosure, such as a particular article configuration, particular additives or ingredients, a particular agent, a particular structural material or component, a particular irradiation, pressure, or temperature condition, or like structure, material, or process variable selected.

In embodiments, the disclosure provides a first vessel such as a cryotube, which permits ejection of the frozen biological material from a first vessel into a liquid medium at, e.g., 37° C. in a second vessel, such as a flask, centrifuge tube, multiwell plate, or like receptacle.

An advantage of ejecting the cryopreserved biological material from the first vessel into 37° C. liquid medium while the material is still frozen is that the first vessel and method of use reduce the risk of rupturing the first vessel. The first vessel is opened before it reaches room temperature, and does not permit any liquid nitrogen that may have seeped into the first vessel to increase the pressure inside the closed first vessel as the liquid nitrogen changes to a gas.

Another advantage is that the first vessel and method of use can reduce the risk of contamination by reducing the risk of vessel or tube rupture and by eliminating the need to place the cryotube into a water bath to thaw. Water from the water bath may also enter the cryotube as it thaws, leading to contamination. Ejecting the biological material from the first vessel can save time by eliminating the step of thawing in the water bath. Another advantage of ejecting the contents of the cryotube into 37° C. liquid medium is that ejecting decreases osmotic and cryoprotectant effects. The first vessel and method can increase the viability of the cryopreserved biological material. Additionally, one can manipulate the cryopreserved cell pellet while it is frozen. This enables cutting the pellet into portions to pool cells while they are frozen. A notch or recess in the bottom rim of the disclosed individual cryovial permits an human operator or a robot to accomplish single-handed opening or closing of the cap when the vial is used in conjunction with a rack or article holster having a detention feature.

The disclosed cryotube articles can have an exterior frame or tube made of, for example, fluoropolymers, polyolefin, polyethylene, and like polymers, or blends of these or like materials. The individual cryotubes can be made to contain various volumes of biological material, such as 1 to 2 mL and 5 to 6 mL of frozen biological materials. The cryotubes in an array format can hold volumes, for example, in the sub-milliliter range. For embodiments with an inner bag or flexible liner, the bag can also be composed of fluoropolymers, polyethylene, polyolefin, blends or laminates of these types of materials, or can be composed of a biodegradable material such as cellulose. The frames or tubes with and without bags or liners can be made by methods, for example, injection molded, blow-molded, thermoformed, and like methods, or combinations of these methods. The tubes and bags can be formed together by the above mentioned methods or formed separately and joined through, for example, over-molding, thermal bonding, welding, adhesive bonding, and like methods, or combinations thereof.

In embodiments that have a biodegradable inner bag or flexible liner, after the cryotube is removed from a cryopreservation storage container, the cap of the article can be removed, and the ejector can be inserted at the opposite end or dry side of the liner to push both the inner bag and contents into the receiving medium instead of just the contents of the bag. A reagent such as cellulase can be added to the medium to aid digestion of the bag to release the biological material contents.

The ejector for pushing the frozen biological material out of the cryotube or cryoplate, and rack or holster for holding the cryotubes during capping and de-capping, can be made from any suitable material including for example, plastic, glass, metal, and like materials, or combinations thereof.

EXAMPLE(S)

The following examples serve to more fully describe the manner of using the above-described disclosure, and to further set forth best modes contemplated for carrying out various aspects of the disclosure. These examples do not limit the scope of this disclosure, but rather are presented for illustrative purposes. The working example(s) further describe(s) how to prepare and use the disclosed articles.

Figure 1B:
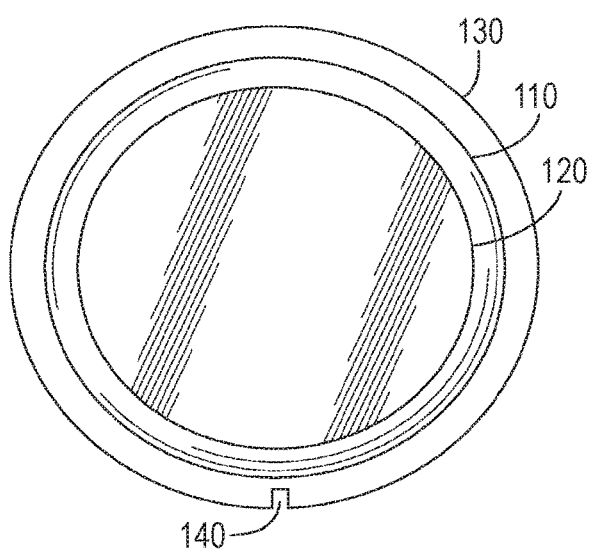
FIG. 1B is a bottom view of the article (100) of FIG. 1A.

Referring to the Figures, FIGS. 1A-B illustrate side and bottom views of an exemplary article (100) such as a cryotube. In embodiments, the cryotube can have an external tube (110) similar to existing commercial cryotubes except that it has no bottom (i.e., bottomless). Internally, there is a bag (120) or flexible liner that can be sealed integrally to the exterior or interior of the tube. When a biological material preparation (125), that has been cryopreserved, is removed from a liquid nitrogen container to thaw, the tube can be taken to a biological hood, where the cap (130) to the cryotube can be removed. An external device or article (150), such as a plunger or ejector, can be used to eject the frozen biological material preparation from the article by insertion of the ejector into the cryotube (110) from the open bottom substantially along a common axis (101), causing the inner bag or liner (120) to deform, sending the frozen biological material preparation into a receiving container of 37° C. liquid medium. The bottom edge or rim of the outer cryotube or external tube (i.e., frame), can have a recessed area (140) that can engage a detention feature on a rack that permits an operator or robot to cap and de-cap a cryotube with one hand or robotic grabber.

Figure 2:
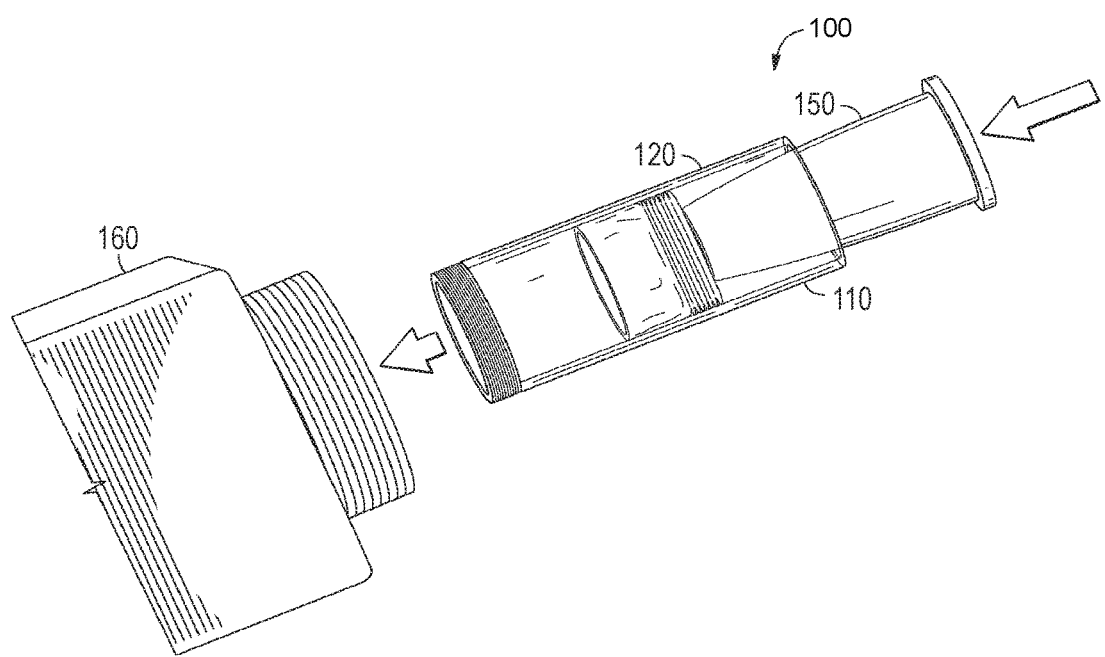
FIG. 2 shows the external ejector article (150) of FIG. 1A being used in combination with the article (100) to eject the biological material into a receiving vessel.

FIG. 2 shows the external ejector article (150) used in combination with the article (100) to eject the biological material into a receiving vessel (160) such as a flask (or centrifuge tube) containing 37° C. liquid medium to thaw the frozen biological material preparation. Alternatively, the entire bag (120), or a portion thereof, can be composed of a biodegradable material and the entire bag, or a portion thereof, can be ejected from the cryotube (110) into the receiving vessel (160) and a liquid medium where the bag can be decomposed as the biological material is thawed.

Figure 3A:
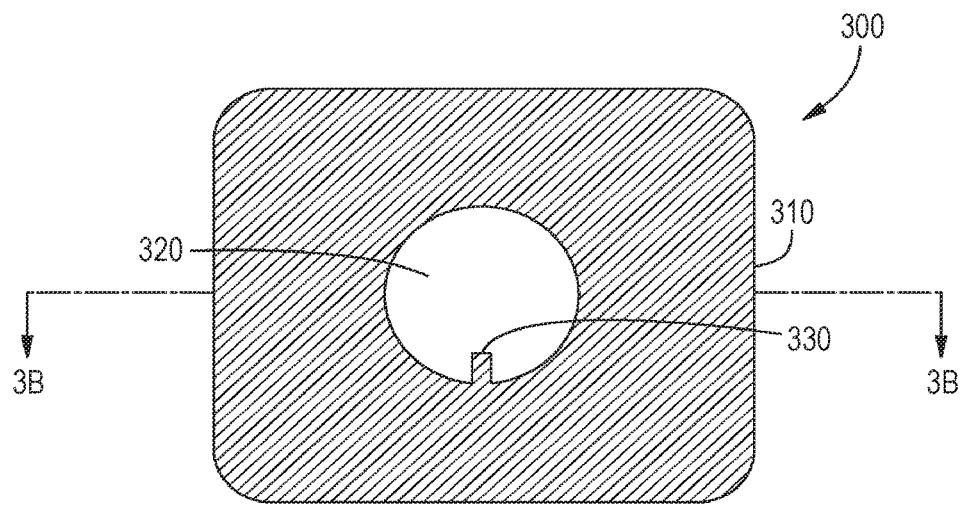
FIGS. 3A and 3B, respectively show a top view (3A) cross-section and side view (3B) cross-section of a holster (300) for a cryotube.
Figure 3B:
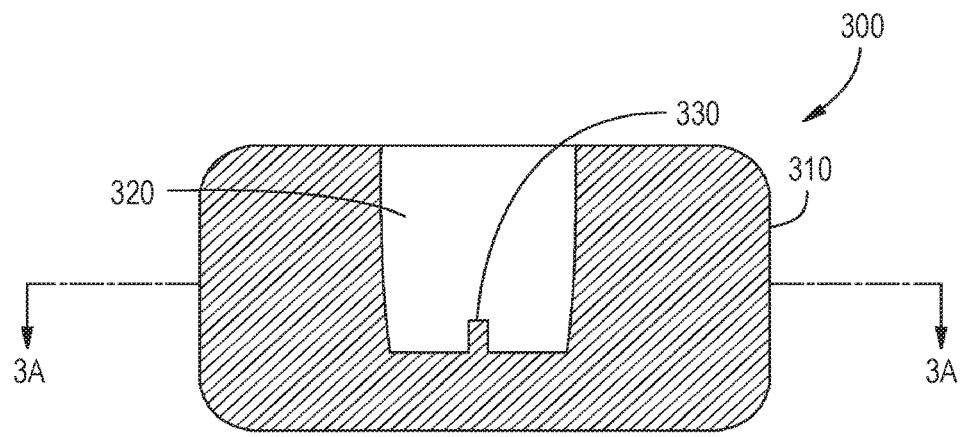

FIGS. 3A and 3B, respectively show a top view (3A) cross-section and side view (3B) cross-section of a holder (300) for a cryotube having, for example, a base or puck (310), a detention area (320), and detention feature (330) such as on a rack or a holster that engages the recessed area (140) on a cryotube to prevent the entire tube from turning, rotating, or otherwise moving as the cryotube is being capped or de-capped. The 3B section in FIG. 3A is shown in FIG. 3B. The 3A section in FIG. 3B is shown in FIG. 3A. A single detent projection (330) for engaging the recessed area for a cryotube is shown. However, the rack or holster can be larger to accommodate many tubes such as from 2 to about 1,000 tubes or more.

Figure 4A:
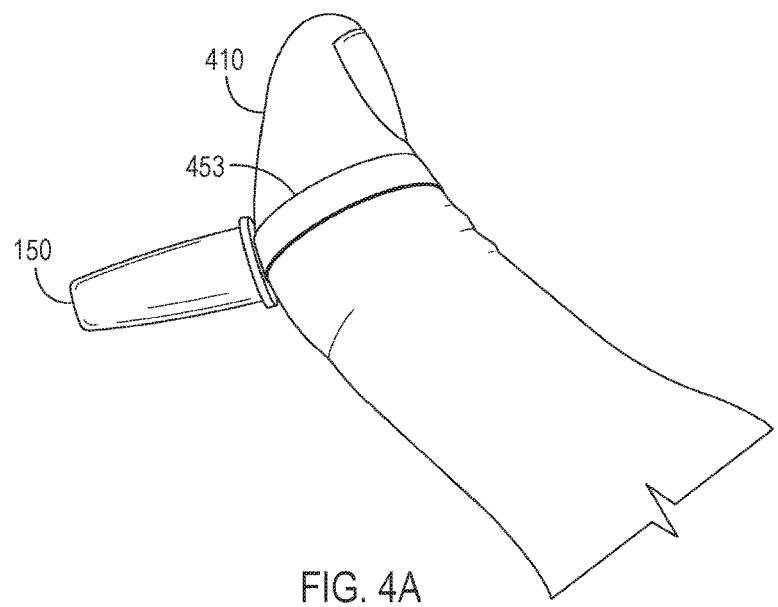
FIGS. 4A-B show some alternative embodiments for the plunger or external ejector (150) article.
Figure 4B:
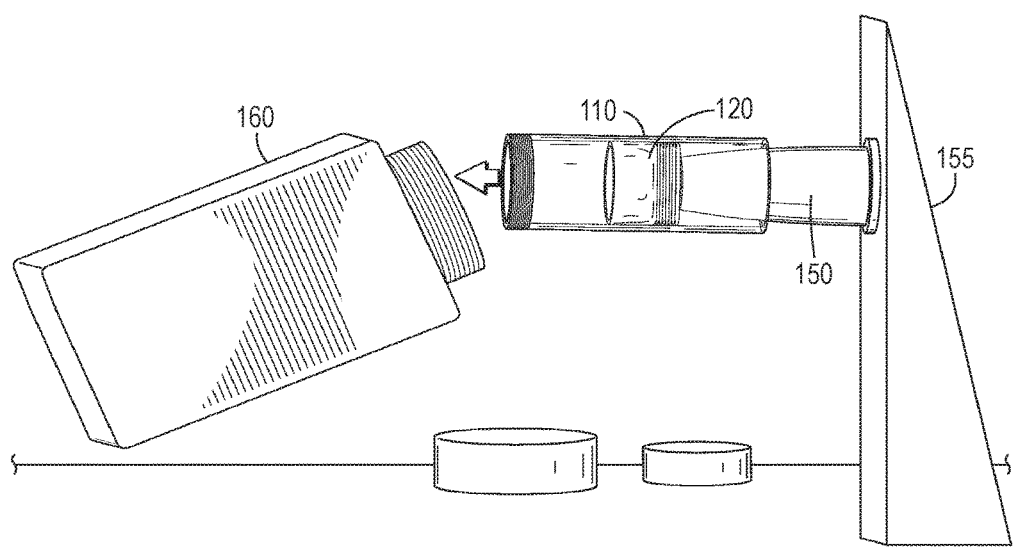

FIGS. 4A-B show some alternative embodiments for the plunger or external ejector article (150). In some embodiments, as shown in FIG. 4A, the ejector can further include, for example, an integral ring (453) that can slide onto a human finger (410). The finger urges the ejector (150) into the cryotube to displace the preparation from the tube (110) into a receiving vessel (160). In other embodiments, the ejector can be, for example, part of an automated device where pushing a button or depressing a trigger moves the ejector in contact with the inner bag (120) of the cryotube. In further embodiments, as shown in FIG. 4B, the ejector (150) can be, for example, part of a stand-alone device or support (155) that can be kept within a biological hood or like containment environment if desired.

Figure 5A:
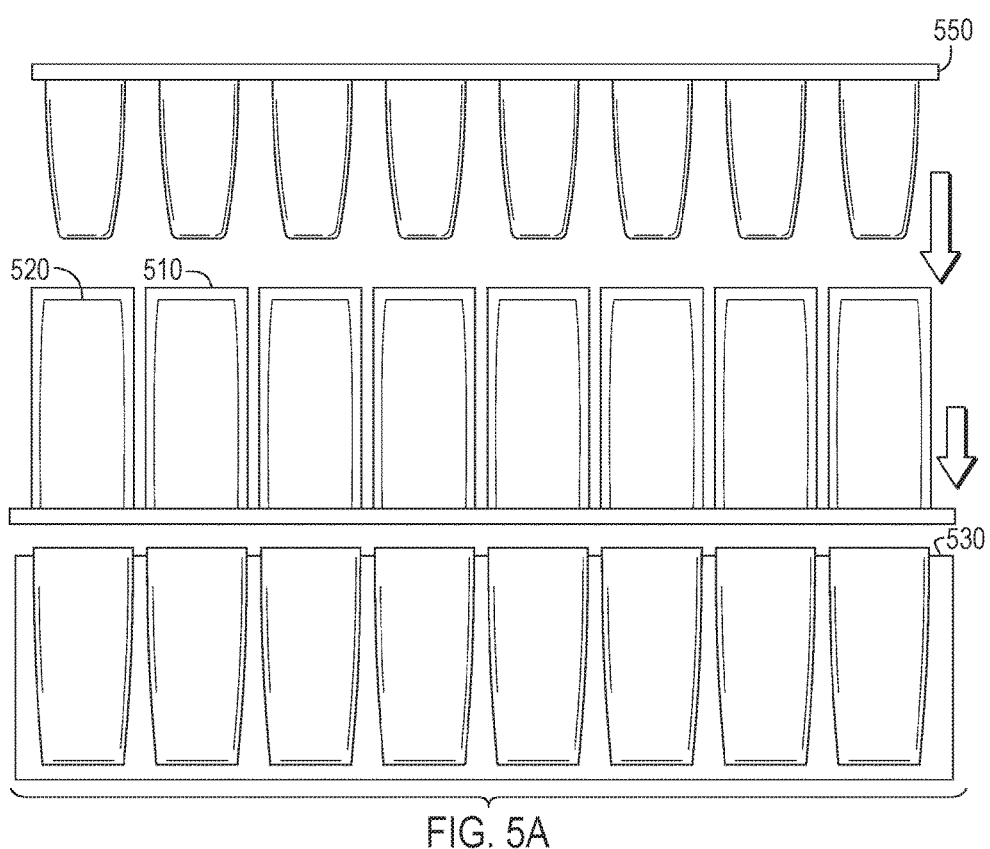
FIGS. 5A and 5B, respectively show an example of a plurality of ganged cryotubes (510) and ganged ejectors (550) used as separates in combination (5A), or used as an integral assembly combination (5B) to displace samples from the cryotubes.
Figure 5B:
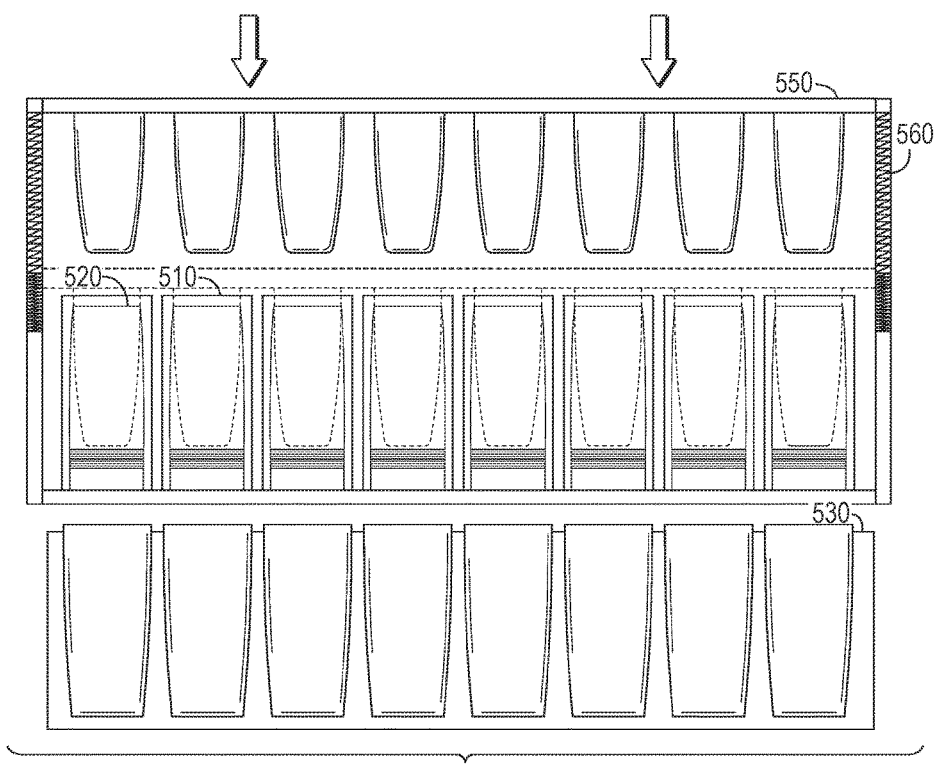

FIGS. 5A and 5B, respectively show embodiments of a plurality of ganged cryotubes (510) and ganged ejectors (550) such as in the form of an array, where the cryotubes and ejectors can be used as separates in combination (FIG. 5A), or used as an integral assembly (5B) combination to displace samples from the cryotubes. The arrays can be any size, but typically can match one or more of the universal multiwell plate (530) formats. In embodiments, the cryotube array (510) can be molded as a multiwell "holey" plate, having an array of integral cryotube inner bags (520). The biological material, preparation, or formulation, can be placed in each inner bag, the plates sealed with a lid or cap (not shown), and then frozen. When the cryotube plate (510) is removed from cryopreservation storage, the lid can be removed, the cryoplate inverted over a multiwell plate (530) of the same or similar format and suitable for use under cryogenic conditions, and the ejector array can be used to deform the inner cryobags forcing the frozen biological material within into a receiving vessel such as a matched multiwell plate (530). When the ganged cryotubes (510) and ganged ejectors (550) is an integral assembly (FIG. 5B), the assembly can be removed from cryopreservation storage, the lid can be removed, the cryoplate inverted over a receiving multiwell plate (530) of the same or similar format and suitable for use under cryogenic conditions, and the integral ejector array can be urged into the "push" end of the cryotubes (510) to simultaneously deform the inner cryobags and simultaneously displace the frozen biological material within each cryotube into a receiving vessel such as a matched multiwell plate (530). The urging or "push" of the ganged ejectors (550) into the cryotubes (510) can be provided by any suitable motive force such as a human hand, a robot, a motor driving a plate in contact with the ganged ejectors, and like source of force, or combinations thereof The applied ejection force displaces the cryopreserved sample from within the cryotube by, for example, sufficient force to collapse the resilient frame member (560) such as a leaf spring or coiled spring.

Figure 6:
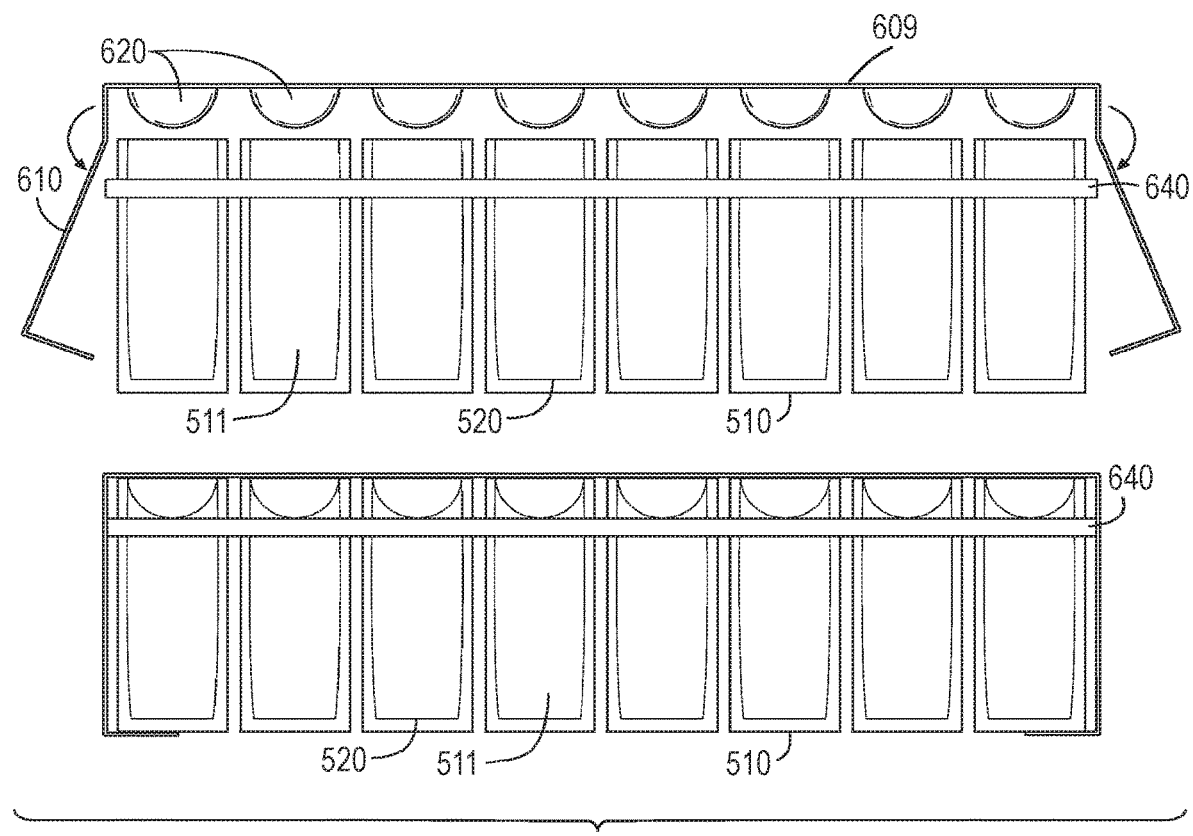
FIG. 6 shows an example of a ganged cryotube array (510) having individual tubes (511) that are joined together by a holder or flat panel (640) and include a ganged closure (609).

FIG. 6 shows a cryotube array (510) having individual tubes (511) that are joined together by a flat panel (640). This cryotube array functions similar to the cryotube array in FIG. 5. This cryotube array can be covered with a closure or lid (609) that can seal the biological material into each cryotube of the array. Silicone or other elastomer buttons (620) that are joined in an array can fill and seal the top of each cryotube in the array. The lid in this example can be held in place with, for example, hinged arms (610) that enclose the plate once the buttons (620) are seated in each cryotube of the array. There are many other types of alternative enclosures that can be used to seal the lid on the cryotube array.

FIGS. 7A-D show front, side, top, and bottom views of a cryotube (700) having a built-in or integrated plunger or ejector (750) and optional closure (130). The cryotube (700) can be a standard size and shape or otherwise. However, the disclosed cryotube can have recessed areas (765) on the frame (710), which can include the external wall or sides of the cryotube, where the segments (760) or legs of the integral plunger are housed. The cryotube having the integral plunger embodiment also has a false bottom just inward of the outer bottom. The integrated ejector (750) is in contact with the inner bag (120). The inner bag can be, for example, attached to and integrally sealed to the interior or exterior of the cryotube (700) near, for example, the top of the cryotube. The cryotube design and structure depicted in FIGS. 7A-D can also have an optional recessed area (740) at or near the bottom rim of the outer tube that can align with a mating detention feature in a cryotube holster or rack. Base (745) includes an aperture (747), which aperture permits the rearranged segments (765) to be pushed through the base and advance the integrated ejector (750) in plunger fashion to act on displacing the contents of the cryotube (700).

Figure 7A:
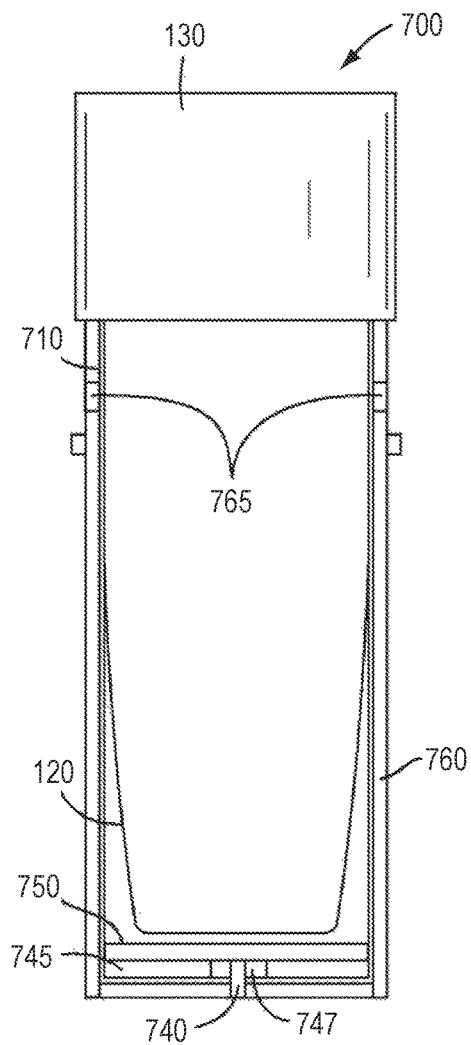
FIG. 7A shows a front view of an exemplary cryotube (700) having a built-in plunger or ejector (750).
Figure 7B:
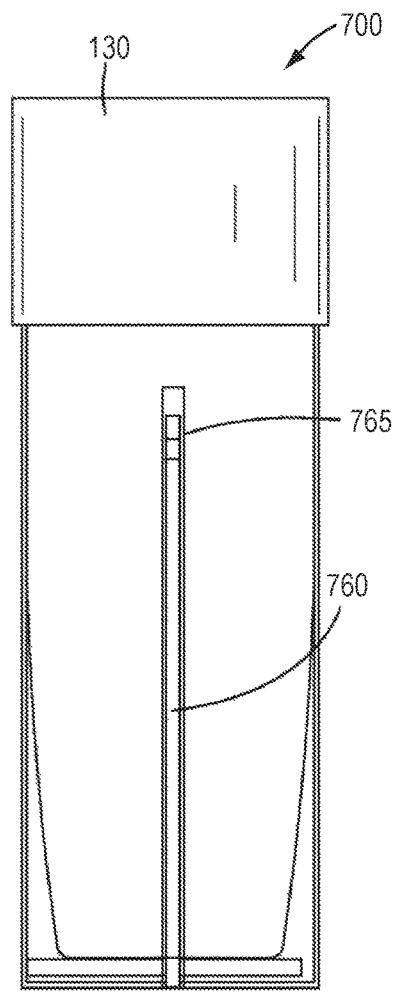
FIG. 7B shows a side view of the cryotube (700) of FIG. 7A.
Figure 7C:
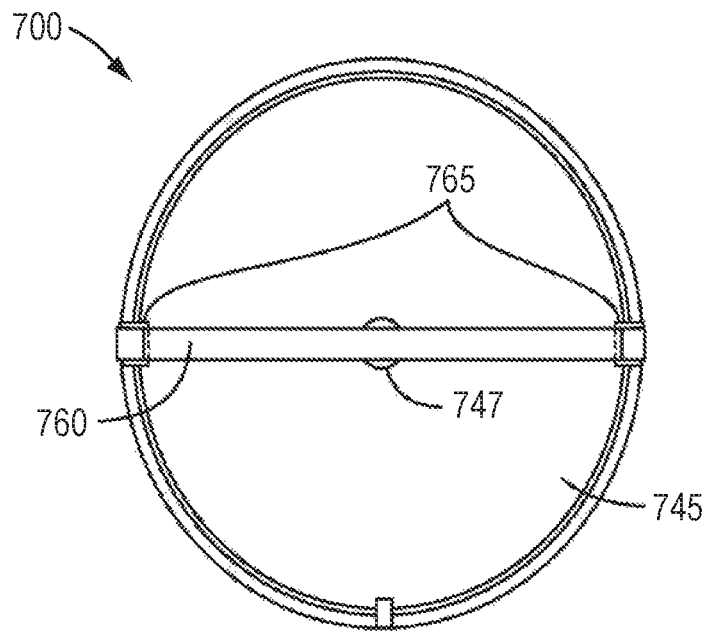
FIG. 7C shows a top view of the cryotube (700) of FIG. 7A.
Figure 7D:
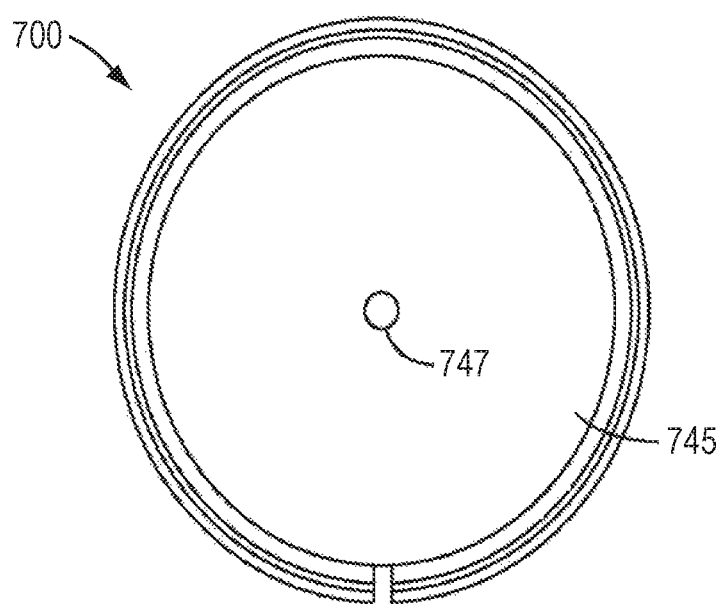
FIG. 7D shows a bottom view of the cryotube (700) of FIG. 7A.
Figure 8A:
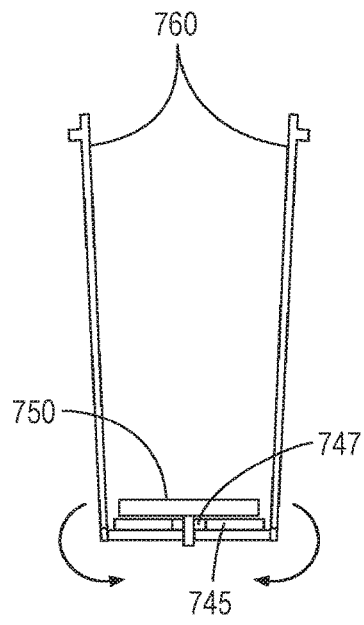
FIGS. 8A-D show the deployment of the plunger segments (760) of the built-in plunger or ejector (750) embodiment of FIG. 7A.
Figure 8B:
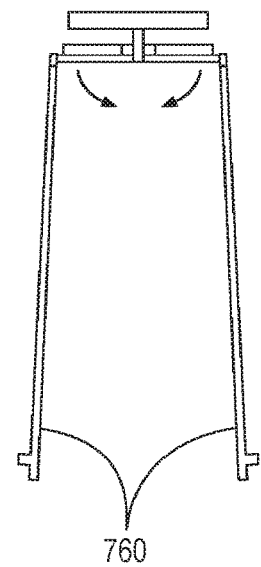
Figure 8C:
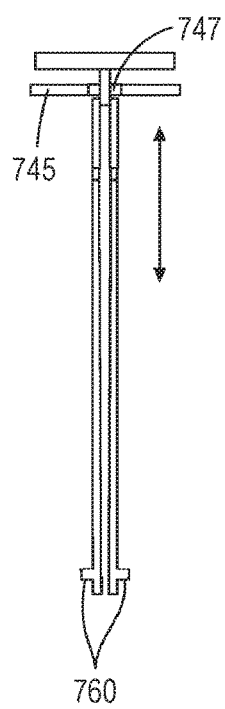
Figure 8D:
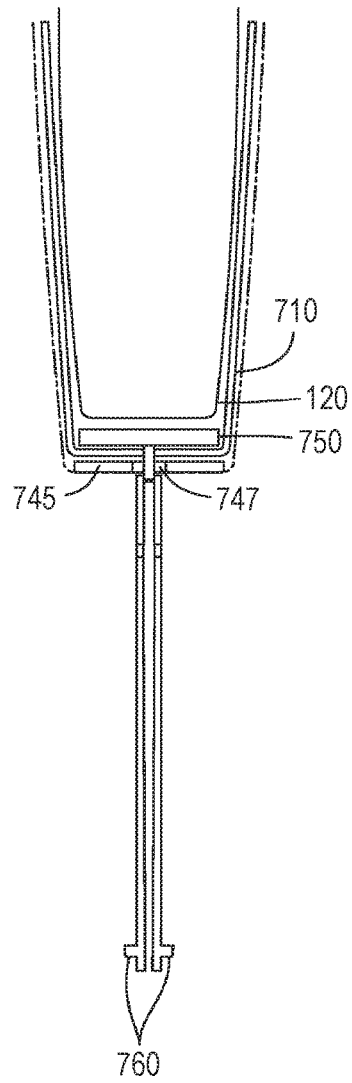

FIGS. 8A-D show the plunger segments (760) of the built-in plunger or ejector embodiment of FIG. 7A. The plunger can unfold in the illustrated sequence of left to right (A-B-C-D) to create the device that can push against the inner bag (120) of the frame (710) to force the frozen contents out of the tube and into the receiving media-containing vessel. Base (745) and aperture (747) are also shown.

Figure 9:
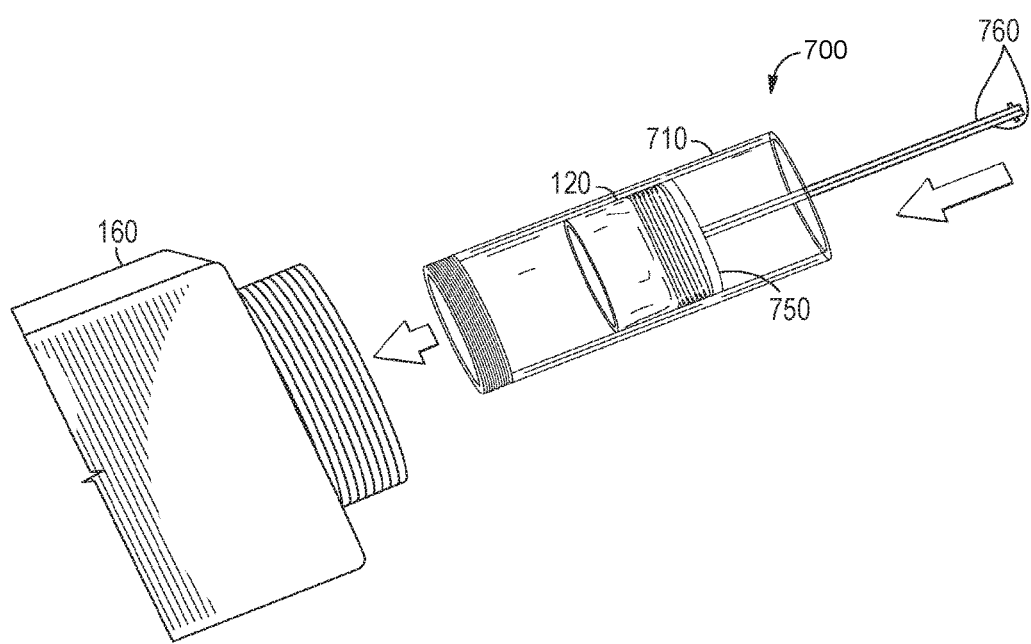
FIG. 9 shows the deployed plunger or ejector (750) and segments (760) of FIG. 7A pushing against the inner bag (120) and deforming the bag to eject the frozen biological material (not shown) into a receiving vessel (160).

FIG. 9 shows the assembled plunger (750) and associated legs (760) being pushed against the inner bag (120) and deforming the bag to eject the frozen biological material (not shown) from the frame (710) into the receiving flask (160) or centrifuge tube containing 37° C. medium.

Figure 10A:
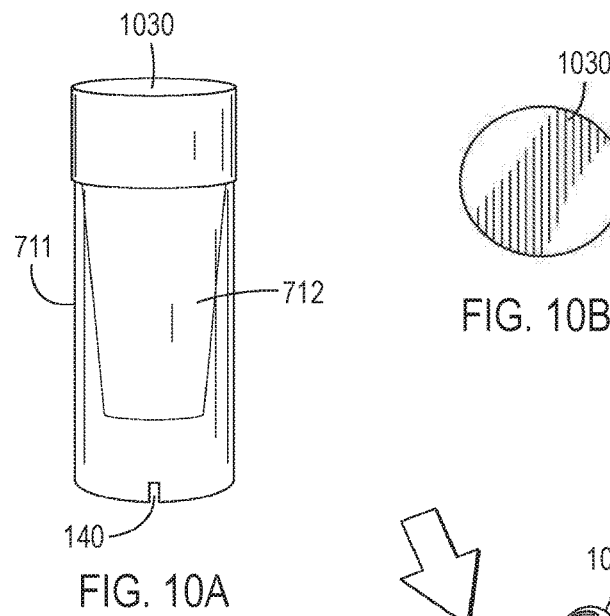
FIG. 10A shows a cryotube having a manually deformable body (711) and chamber structure of oblong geometry.
Figure 10B:
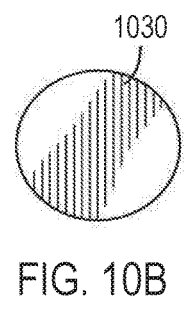
FIG. 10B shows a top view of the circular closure (1030) depicted in FIG. 10A.
Figure 10C:
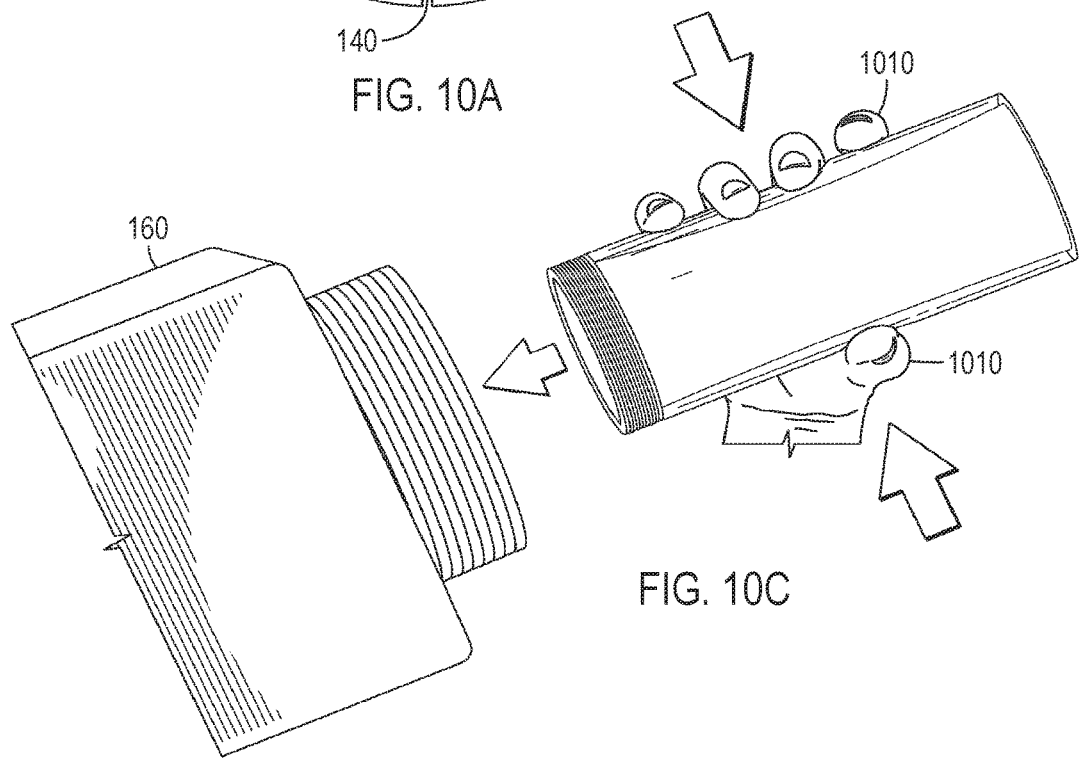
FIG. 10C shows the operation of the cryotube (711) of FIG. 10A.

FIG. 10A shows a cryotube having an oblong or elongated geometry. The cryotube can have, for example, an oval, ovoid, or egg shape, or a circle or circular shape when viewed in cross-section. The cryotube wall material can be selected to be mechanically, reversibly deformable so that, after de-capping (e.g., a circular closure (1030) as depicted in FIG. 10B) or opening the cryotube, and compressing or squeezing with a human hand (1010) as shown in FIG. 10C, or like instrumentality, on the opposing sides of the cryotube the body (711) deforms and dislodges the frozen biological material contents from cavity (712), such as a conic, ovoid, circular, or like shape. This operation enables the frozen material to slide out of the tube and into the receiving vessel of 37° C. medium. This design can also have a recessed area (140) at the bottom rim of the deformable body (711) that can align with a detention feature in a cryotube rack or holster (not shown) and as discussed above. The cryotube of FIG. 10 can, for example, transition from a conic, ovoid, or circular body to a circular opening of a different diameter so as to enable the use of standard closure items, such as a screw cap or snap-fit cap.

Materials and Methods

Plastic cryotubes, cryovials, or both, are typically injection molded products made on multi-cavity molds. Cryotubes can be, for example, molded from at least one of polypropylene, polystyrene, polyethylene, polymethyl methacrylate, polyvinyl chloride, polymethyl pentene, polycarbonate, polysulfone, polystyrene copolymer, polypropylene copolymer, cyclic olefin copolymer, fluoropolymer, poly(styrene-co-maleic anhydride) or polyamide, and like polymers or copolymers of these or related materials. The disclosed cryotubes, cryowell plates, and devices to aid ejection of frozen cells from the inner bags may also be molded or thermoformed from similar polymer materials. The disclosed vessels having an inner bag can have outer cryotubes or cryowell plates that can be, for example, over-molded onto the inner bags, or the bags may attached subsequent to injection molding, using any attachment methods known in the art, such as thermal welding, adhesive bonding, ultrasonic welding, and like methods, or combinations thereof. The inner bags can be produced by, for example, thermoforming or heat-sealing films or multilayer-film laminates. Tubing can also be extruded, cut and sealed to form bags. Bags can be made from, for example, polyethylene, polypropylene, perfluorinated polymers, polyester, polydimethylsiloxane, and like materials, including blends and laminates of these materials, and combinations thereof. Alternatively, in embodiments, the inner bag can be composed of a biodegradable material such as cellulose.

The disclosed vessels can be used in the same manner as commercially available cryotubes. Typically, cells to be stored by cryopreservation are harvested, collected in a centrifuge tube and subjected to centrifugation to pellet the collected cells. The medium is removed from the centrifuge tube following centrifugation and the cells forming the pellet resuspended in medium containing a cryoprotectant such as dimethylsulfoxide (DMSO), glycerol, serum, and like materials, or combinations thereof. The cells in cryoprotection medium are placed into the inner bag of a cryotube or cryoplate vessel. The cryotube is capped, or in the instance of a cryowell plate, the plate is lidded. The cryotube or cryowell plate can then be placed in, for example, a programmable rate controlled freezer or suitable alternative such as a polystyrene box, or alcohol bath (e.g., a Nalgene® 'Mr. Frosty') which can be used in a −80° C. freezer for up to 24 hours prior to transfer to gaseous phase nitrogen to promote cooling at a rate of, for example, about 1 to 3° C./min.

When the frozen cells are ready to be thawed and used, the cryotube is removed from the gaseous phase nitrogen storage. The cryotube is uncapped and the frozen pellet in the cryotube is ejected from the cryotube, using the ejector member or like device. The ejector member or ejector article ("ejector") can be inserted in the base of the cryotube, and pushed to make contact with the internal bag containing the frozen pellet. The pellet is urged out or projected out of the cryotube bag and into a prepared container of fresh culture medium at 37° C., where the pellet is immediately thawed. For the cryowell plate, the lid is removed from the plate and the plate is inverted over a multiwell plate of the same or greater well number and dimensions as the cryowell plate, and each well contains fresh culture medium at 37° C. The cryowell plate ejector-array device can be used in the same manner as the cryotube ejector. In the instance of cryotubes having an ovoid or oval cross-section, the vertices of the oval can be depressed to release the frozen pellet from within the cryotube and then inverted to send the pellet into a receiving vessel containing medium at 37° C.

This procedure differs from the standard procedure in that the cells in the cryotube or cryowell plate are not placed into a 37° C. water-bath to thaw prior to placement into the awaiting fresh medium container. Being able to eject the pellet in a frozen state directly into 37° C. medium avoids the time spent with the cryotube in a water-bath to thaw the cells, decreases the potential for contamination of the cells by the water-bath, and increases the viability of the cells by quickly diluting the concentration of the cryoprotectant.

The disclosure has been described with reference to various specific embodiments and techniques. However, it should be understood that many variations and modifications are possible while remaining within the scope of the disclosure.

What is claimed is:

1. A cryopreservation article for cryopreservation of a biological sample, the article comprising:
    a plurality of frames, each frame having an interior cavity;
    a plurality of integral ejectors comprising a plurality of ganged ejectors aligned with and attached to the plurality of frames, wherein the plurality of ganged ejectors is separated from the plurality of frames by at least one spring member; and
    a flexible liner situated within the interior cavity;
    wherein each frame comprises:
        a first open end configured for receiving the biological sample in liquid form into the flexible liner, and
        a second open end comprising an integral ejector of the plurality of integral ejectors configured to engage with the flexible liner and dispense the biological sample in solid form from a location within the interior cavity, and
    wherein at least a portion of the integral ejector is configured to move through the second open end toward the first open end for dispensing the biological sample; and
    wherein the frame and flexible liner can withstand freezing at a liquid nitrogen temperature.

2. The article of claim 1, wherein each frame in the plurality of frames is a hollow cylinder or hollow conic having first and second open ends.

3. The article of claim 1, wherein an external wall of each frame comprises at least a portion of the integral ejector.

4. The article of claim 3, wherein at least a portion of the integral ejector is positioned in an external recess of the exterior wall.

5. The article of claim 4, wherein the integral ejector is a plunger.

6. The article of claim 1, wherein the integral ejector comprises at least one retractable member.

7. The article of claim 1, further comprising a closure member for reversibly sealing the biological sample in the interior cavity.

8. The article of claim 7, wherein the closure member comprises at least one of:
    a screw cap adapted to engage screw threads on the frame;
    a press fit plug having an optional strap to engage the frame, or
    a combination thereof.

9. The article of claim 1, wherein the flexible liner is over-molded to the frame.

10. The article of claim 1, wherein the flexible liner comprises a biodegradable liner.

11. The article of claim 1, wherein a diameter of the first open end is equal to or greater than a maximum diameter of the interior cavity.

12. A cryopreservation article for cryopreservation of a biological sample, the article comprising:
    a frame having an interior cavity; and
    a flexible liner situated within the interior cavity;
    wherein the frame comprises:
        a first open end configured for receiving the biological sample in liquid form into the flexible liner, and
        a second open end comprising an integral ejector configured to engage with the flexible liner and dispense the biological sample in solid form from a location within the interior cavity, and
    wherein the frame and flexible liner can withstand freezing at a liquid nitrogen temperature,
    wherein at least a portion of the integral ejector is configured to move through the second open end toward the first open end for dispensing the biological sample,
    wherein an external wall of the frame comprises at least a portion of the integral ejector,
    wherein at least a portion of the integral ejector is positioned in an external recess of the exterior wall, and
    wherein the integral ejector is a plunger, wherein the portion of the integral ejector that is positioned in the external recess of the exterior wall comprise legs of the plunger, the legs being connected to a head of the plunger, and wherein the legs are rotatable about the head of the plunger to move out of the external recess to a position where the head of the plunger is disposed between the interior cavity and the legs.

* * * * *

UNITED STATES PATENT AND TRADEMARK OFFICE
CERTIFICATE OF CORRECTION

PATENT NO. : 11,008,157 B2
APPLICATION NO. : 15/419678
DATED : May 18, 2021
INVENTOR(S) : Jessica Monique Brown et al.

Page 1 of 1

It is certified that error appears in the above-identified patent and that said Letters Patent is hereby corrected as shown below:

On the Title Page

In Column 1, item (72), Inventors, Line 6, delete "Portmouth," and insert -- Portsmouth, --, therefor.

On page 3, in Column 1, item (56), Other Publications, Line 6, delete "Catalong," and insert -- Catalog, --, therefor.

Signed and Sealed this
Third Day of August, 2021

Drew Hirshfeld
*Performing the Functions and Duties of the
Under Secretary of Commerce for Intellectual Property and
Director of the United States Patent and Trademark Office*